United States Patent
Schöni

[11] Patent Number: 5,956,994
[45] Date of Patent: Sep. 28, 1999

[54] TEST APPARATUS FOR LINEAR TEST MATERIAL SUCH AS YARN OR THE LIKE

[75] Inventor: Markus Schöni, Schwerzenbach, Switzerland

[73] Assignee: Zellweger Luwa AG, Switzerland

[21] Appl. No.: 09/082,610

[22] Filed: May 20, 1998

[30] Foreign Application Priority Data

May 20, 1997 [CH] Switzerland ............................ 1164/97

[51] Int. Cl.⁶ .................................................. G01L 5/04
[52] U.S. Cl. ................................................................ 73/159
[58] Field of Search ............................... 73/159, 862.391, 73/862.42, 862.451, 862.471

[56] References Cited

U.S. PATENT DOCUMENTS

| | | | |
|---|---|---|---|
| 4,171,640 | 10/1979 | Van Mastrigt | 73/862.472 X |
| 4,817,424 | 4/1989 | Pellatiro | 73/159 |
| 5,178,007 | 1/1993 | Ghorashi et al. | 73/159 |
| 5,649,448 | 7/1997 | Koskimies et al. | 73/159 |
| 5,684,707 | 11/1997 | Rogowski | 73/159 X |

FOREIGN PATENT DOCUMENTS 2 192 722  11/1990  United Kingdom .

*Primary Examiner*—George Dombroske
*Assistant Examiner*—Jewel V. Thompson
*Attorney, Agent, or Firm*—Burns, Doane, Swecker & Mathis

[57] ABSTRACT

The invention relates to a test apparatus (1) with an end face (11) in front of which a yarn, roving or sliver is moved along in the longitudinal direction in order to test properties, with a plurality of zones of action (8, 9, 10) for producing a respective interaction between the test apparatus and the test material. In order to be able to provide a simple path, which is independent of the number of zones of action, for the yarn, roving or sliver, the yarn, roving or sliver is guided at least approximately in one plane transverse to the end face.

4 Claims, 2 Drawing Sheets

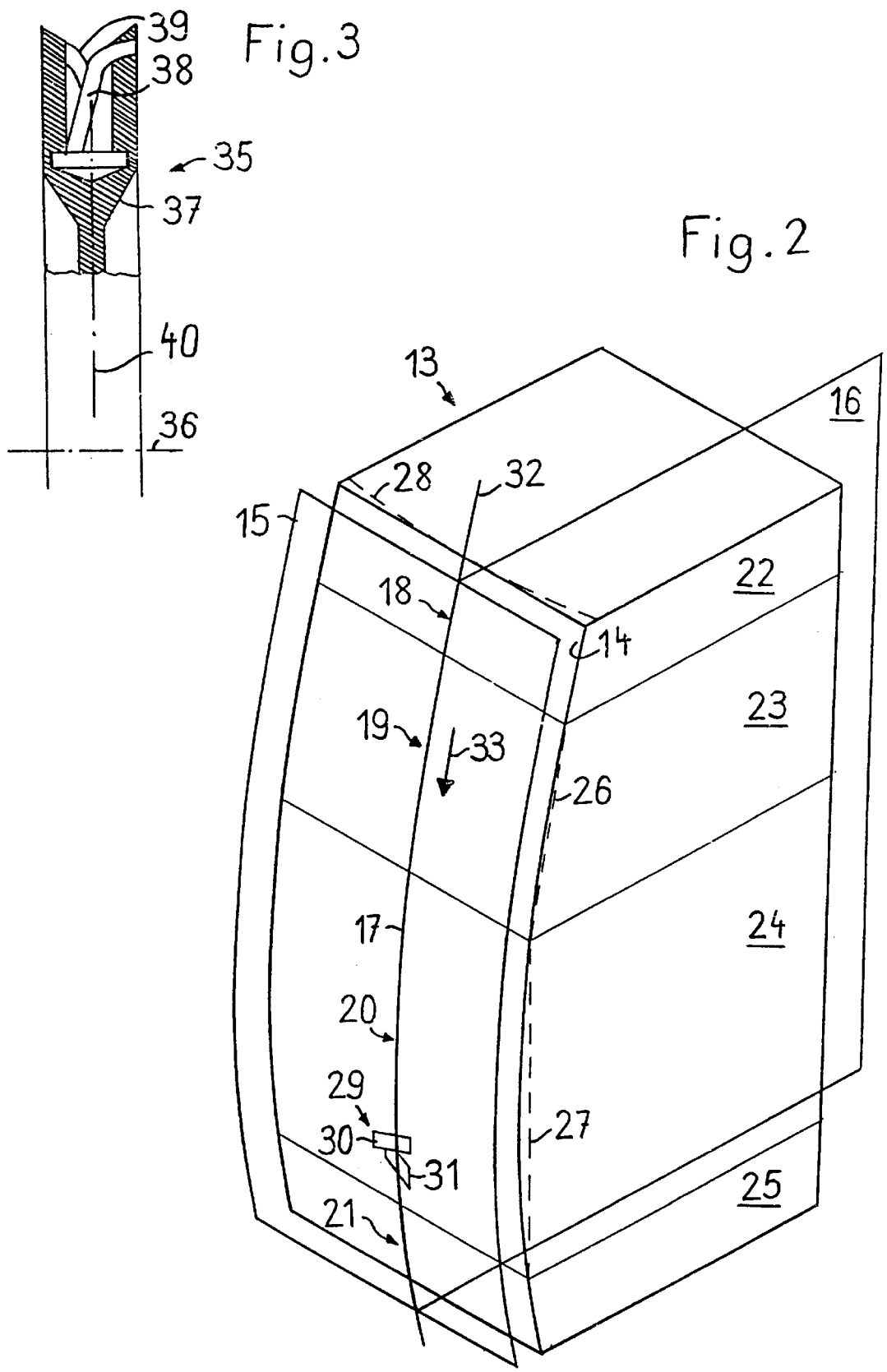

TEST APPARATUS FOR LINEAR TEST MATERIAL SUCH AS YARN OR THE LIKE

FIELD OF THE INVENTION

The invention relates to a test apparatus for testing properties of a linear test material moved along in its longitudinal direction in front of an end face, with a plurality of zones of action for producing a respective interaction between the test apparatus and the test material.

BACKGROUND

The end face of known test apparatus of this kind is either straight or composed of angled sections, so that it may be straight or, considered as a whole, curved, for example, in the direction of movement of the test material, that is, for example, the yarn, roving or sliver. This applies particularly if the test apparatus is composed of modules which each occupy a section of the end face. Such test apparatus is shown and described, for example, in Great Britain patent GB 2 192 722, the disclosure of which is incorporated herein by reference.

It is also usual to provide guides for guiding the yarn, roving or sliver separately in two directions, namely: parallel and perpendicular to the end face. The end face may be divided into different zones of action such as, e.g. a test or measurement zone, in which properties of the yarn, roving or sliver are tested or measured, a guide zone, in which means for orienting and guiding the yarn, roving or sliver are provided, and into a drive zone, in which means for driving or moving the yarn, roving or sliver are provided. These zones of action are usually laterally staggered, so that the test material follows a variable, bent path (viewed in the direction of the end face). Or, in other words, the yarn, roving or sliver is directed by guides in the region of the measurement zone into a path which outside of this region adopts a different course which does not constitute a natural continuation of the path in this region or in the measurement zone.

The disadvantages which this arrangement entails lie in the fact that in this case guides always produce deflections which may affect the properties of the yarn, roving or sliver. For example, the hairiness of a yarn may be changed to a greater or lesser degree according to the angle at which the yarn loops round the guide and according to the radius of the guide. Furthermore, the zones of action which are to follow one another in the longitudinal direction of the yarn, roving or sliver must be laterally staggered such that the action of guides of preceding and following zones of action is not impaired. This either results in the yarn, roving or sliver being laterally displaced by a certain amount or deflected for each zone of action or in the necessity of providing a particularly large number of guides. In addition, the guides are subjected to high loads and in turn load and deform the cross section of the yarn, roving or sliver.

SUMMARY OF THE INVENTION

The invention provides a test apparatus of the above-mentioned type which does not have these disadvantages and provides a simple path, which is independent of the number of zones of action, for the test material.

This is achieved according to the invention by guiding the test material at least approximately in one plane transverse to the end face. In this case this plane extends radially (when the end face is curved twice) or perpendicularly to the end face. Guides which define a path for the test material are disposed such that the test material is substantially only deflected in the plane, not in the end face or a face parallel thereto. The guides are formed such that the test material is guided over a region of its circumference and is preferably centered in the plane. This is in contrast with known guides, which ideally only contact and guide the test material along a single line. This can be achieved by a rounded guide partly encircling the test material or by a plurality of guide faces which are inclined towards one another or cross one another. The guide faces are preferably straight or only slightly curved and cross one another or intersect in the above-mentioned plane.

The advantages which are thus achieved lie in particular in the fact that the test material is only slightly affected and loaded. Any desired number of modules for each zone of action may now be disposed in any desired order. The automatic introduction of the test material is equally simplified, for the test material can be delivered in one plane and the guides are easily accessible in this plane. As there are no deflections, only relatively low drive forces are accordingly required for the test material.

BRIEF DESCRIPTION OF THE DRAWINGS

The invention is explained in detail in the following on the basis of an example and with reference to the accompanying figures, in which FIG. 2 shows a simplified view of substantial elements of the test apparatus and Figure 3 shows a component part of the test apparatus.

DETAILED DESCRIPTION OF PREFERRED EMBODIMENT

Figure 1:
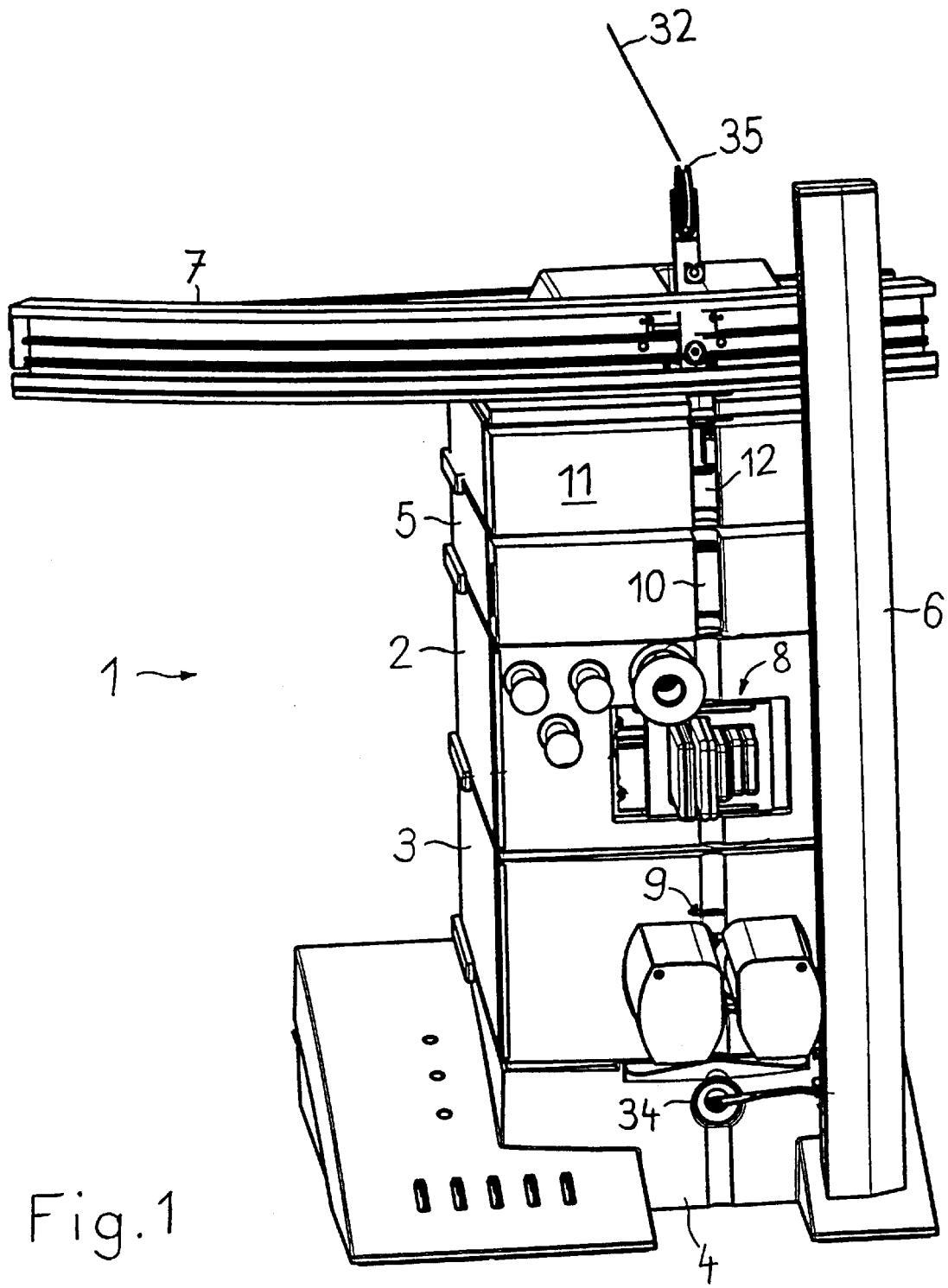
FIG. 1 shows a view of a test apparatus according to the invention.

FIG. 1 shows a view of a test apparatus 1 according to the invention by means of which properties of a test material such as, e.g. a yarn, roving or sliver, can be tested or measured. These properties are, for example, uniformity of mass or cross section, hairiness, presence of foreign substances in the test material, tensile strength, twist, etc. The test apparatus 1 comprises various parts, for example various modules such as a test module 2, a drive module 3, a draw-off module 4, a guide module 5, a delivery device 6 and a test material change-over device 7. These parts and modules all act on the test material in a certain manner in predetermined zones of action. The figure shows, for example, a zone of action 8, in which test or measurement values are acquired, a zone of action 9, in which the test material is driven, and a zone of action 10, in which the test material is guided. A plurality of these zones of action, in which an interaction takes place between the test material and the test apparatus 1, are provided in regions of an end face 11, that is in front of or in the latter, and particularly along a passage 12, which extends over a plurality of modules 2, 3, 4, 5.

FIG. 2 shows a test apparatus according to FIG. 1, again in a simplified, diagrammatic view in order that certain characteristics may be distinguished more clearly. The test apparatus 13, which is shown here without a test material change-over device or a delivery device, has an end face 14, and a parallel face 15 is imagined and drawn parallel to the end face 14. A plane 16 is imagined substantially perpendicular to the end face 14 and to the parallel face 15 and forms an intersection line 17 with the parallel plane 15. This line 17 forms a path for the test material, in particular the yarn, roving or sliver, along which it can move. Various zones of action 18, 19, 20 and 21, in which an interaction takes place between the test apparatus and the test material in the path 17, are provided alongside this path or intersection line 17. Interactions of this kind are, for example, the guidance, measurement or testing, driving or movement of the test material, etc. Appropriate means are accordingly disposed in these zones of action. These are, for example, guides for the yarn, roving or sliver in the zones of action 18 and 21. This is, for example, a measurement unit, in particular an optically or capacitively operating uniformity sensor, a hairiness sensor or a foreign substance sensor, etc., in the zone of action 19. This may be, for example, a drive device, which pulls the yarn, roving or sliver 2 in the direction of an arrow 33, etc., in the zone of action 20. The test apparatus 1 may also be divided into individual modules 22, 23, 24 and 25, which are replaceable or interchangeable, according to the zones of action. Instead of being arched, the individual modules 22 to 25 may also have straight end faces, as indicated for the modules 23 and 24 by the broken lines 26 and 27, which indicate sections of the end face 14 which are inclined towards one another. Together they form an approximately curved end face. The end face could, however, also be curved as indicated by the broken line 28. An end face curved twice could be produced in this way. In such a case the plane 16 would have to be located radially or at least approximately perpendicular to a face tangential to the end face. A straight end face and a curved parallel face are, however, also possible. It is therefore not essential for the parallel face 15 to extend absolutely parallel to the end face 14, although it is disposed in front of the end face 14. A plurality of guides are provided along the path 17, one of which is designated by 29 and represented diagrammatically here. The guide 29 preferably consists of two guide faces 30, 31, which are inclined towards one another and disposed, for example, in the form of a V. The guide faces 30, 31 may be plane or slightly curved and disposed above or next to one another, so that at least parts thereof cross or intersect in the plane 16.

FIG. 3 shows a part of a deflector wheel 35, as provided to feed the test material into the passage 12 (FIG. 1). The center plane 40 of this deflector wheel lies substantially in the plane 16 (FIG. 2). This deflector wheel 35 comprises a wheel body 37, which is mounted such that it can rotate freely about an axis 36. Guide webs 38, 39, which are inclined one behind the other at the circumference, are provided to guide the test material. These are spaced apart, so that the test material runs straight between the guide webs and is not supported. Deflector wheels of this kind are known under the name "feed wheels" and produced, for example, by the firm Ascotex Limited in Burnley, England.

The test apparatus operates as follows:

A test material 32, in particular a yarn, roving or sliver, is drawn off a bobbin by the test material change-over device 7 via the deflector wheel 35 in a manner which is known per se and therefore not shown in detail here and positioned in front of or in the passage 12 by the delivery device 6. In this position the test material ideally runs along a straight path in one plane 16 and therefore, at least from one aspect, parallel to the plane 16, in front of the modules 2 to 5 (FIG. 1). All the guides 29 along the path 17, the deflector wheel 35 and all the zones of action 18 to 21 are also oriented such that,
as far as possible, this path 17 extends in one plane. The test material is moved in the direction of an arrow 33 to carry out a test or measurement, this direction corresponding approximately to the longitudinal direction of the yarn, roving or sliver. The movement is produced by the drive module 3. As a result of this special orientation of the guides and zones of action, the delivery device 6 can introduce the test material with an arm 34 by a simple rectilinear movement along the passage 12, the test material automatically falling correctly into the guides and zones of action. Because the end face 11 is preferably curved, as indicated in FIG. 2, this introduction of the test material is effected particularly reliably, as the test material then rests securely on all the guides along the path 17. It is in this respect of no importance whether the test material runs exactly in the end face 11, 14, exactly in the parallel face 15, in between, or even behind the end face 11, 14. The important factor is for it to run substantially in one plane 16. This preferably extends radially or perpendicularly to the end face 11, 14. The specially formed deflector wheel 35 ensures that the test material is not subject to any friction and that it enters the plane 16 steadily, so that oscillations in the longitudinal direction are also damped.

It is particularly important for the test material to run in the zones of action in the plane 16 and for the zones of action to be oriented according to this plane.

What is claimed is:

1. Test apparatus for testing properties of a test material (32) moved along in front of an end face (14) in the longitudinal direction (33), with a plurality of zones of action (18, 19, 20, 21) for producing a respective interaction between the test apparatus and the test material, said apparatus comprising guide means for guiding the test material in a path (17) substantially in one plane (16) transverse to the end face in the zones of action, said guide means including guide faces (30, 31) disposed one behind the other in the direction of movement of the test material and being inclined in opposite directions which cross one another in the plane (16).

2. Test apparatus according to claim 1, including a deflector roller (35) for the test material moving along the path (17).

3. Apparatus for testing linearly elongated test material such as a yarn or the like, comprising a plurality of modules for interacting with said test material as such material is moved in its lengthwise direction, said modules being assembled together to prestab an apparatus end face, guide means establishing a linear test material path in front of said end face substantially in one plane transverse to said end face, and means for moving the test material lengthwise through said path in said plane, said guide means including oppositely inclined guide faces disposed one behind the other in the direction of movement of said test material and each intersecting said plane substantially at the location of said linear test material path.

4. Apparatus according to claim 3, including a deflector roller mounted for rotation about an axis substantially perpendicular to said plane and having at its periphery multiple sets of oppositely inclined guide faces disposed one behind the other and intersecting said plane substantially at the location of said test material path for guiding said linear test material into said path.

* * * * *